United States Patent [19]

Dobson

[11] Patent Number: 5,393,918
[45] Date of Patent: Feb. 28, 1995

[54] HIGH YIELD PROCESS FOR THE PRODUCTION OF METHACRYLIC ACID ESTERS

[75] Inventor: John C. Dobson, Lansdale, Pa.

[73] Assignee: Rohm and Haas Company, Philadelphia, Pa.

[21] Appl. No.: 160,697

[22] Filed: Dec. 2, 1993

[51] Int. Cl.$^6$ ............................................. C07C 67/20
[52] U.S. Cl. ................................. 560/215; 560/187; 560/179
[58] Field of Search ........................................ 560/215

[56] References Cited

U.S. PATENT DOCUMENTS

| | | | |
|---|---|---|---|
| 2,416,756 | 3/1947 | Jilk | 560/215 |
| 2,786,739 | 3/1957 | Eric et al. | 560/215 |
| 3,027,328 | 3/1962 | Hüter | 560/215 |
| 4,529,816 | 7/1985 | DeColibes et al. | 560/212 |
| 5,087,736 | 2/1992 | Higuchi et al. | 560/215 |

FOREIGN PATENT DOCUMENTS

| | | |
|---|---|---|
| 379691 | 8/1990 | European Pat. Off. . |
| 407811 | 1/1991 | European Pat. Off. . |
| 429800 | 6/1991 | European Pat. Off. . |
| 45/8850 | 3/1970 | Japan . |
| 17204 | 5/1971 | Japan . |
| 17205 | 5/1971 | Japan . |
| 36723 | 9/1972 | Japan . |
| 3264551 | 11/1991 | Japan . |
| 2086892 | 5/1982 | United Kingdom . |
| 2208864 | 4/1989 | United Kingdom . |

*Primary Examiner*—Paul J. Killos
*Attorney, Agent, or Firm*—Terence Strobaugh; Jordan Driks; Thomas Rogerson

[57] ABSTRACT

This invention provides a method for producing $\alpha,\beta$-unsaturated carboxylic acid esters in high yield from acetone cyanohydrin and sulfuric acid through the reduction of reaction side products and the recycling of process intermediates.

9 Claims, No Drawings

HIGH YIELD PROCESS FOR THE PRODUCTION OF METHACRYLIC ACID ESTERS

BACKGROUND OF THE INVENTION

This invention relates to a method for producing high purity methacrylic acid esters in high yield. A number of commercial processes are practiced for the production of such esters including sulfuric acid treatment of acetone cyanohydrin, two stage oxidation of isobutylene or t-butyl alcohol, and liquid phase catalytic condensation of propionaldehyde with formaldehyde.

A typical commercial cyanohydrin process is described in U.S. Pat. No. 4,529,816 ("816") for the production of methyl methacrylate ("MMA"). In this process, acetone cyanohydrin ("ACH") is (1) hydrolyzed by sulfuric acid to produce α-hydroxyisobutyramide ("HIBAM") and its sulfate ester, α-sulfatoisobutyramide ("SIBAM"); (2) the HIBAM and SIBAM are thermally converted to 2-methacrylamide ("MAM") and a small amount of methacrylic acid ("MAA"); which is then (3) esterified with methanol to produce MMA (residual HIBAM is esterified to methyl α-hydroxyisobutyrate ("MOB")). Also disclosed in '816 is an improvement to the general process for producing MMA wherein the MOB present is isolated and returned to the process between the thermal conversion and esterification steps.

The thermal conversion step in '816 is conducted at a sufficiently high temperature and for a sufficiently long time to maximize MAM formation from HIBAM and SIBAM prior to esterification. The thermal conversion of SIBAM is more facile than the thermal conversion of HIBAM. One objective of '816 is to obtain the maximum yield of MAM and MAA at this step. MAA is a co-product of the thermal conversion step and is also converted to MMA during esterification. In addition, '816 specifies that care must be taken when returning isolated MOB into the process between the thermal conversion and esterification steps such that the sulfuric acid strength is maintained at about 97-100% and the mole ratio of free sulfuric acid to MOB is maintained between 4 and 40.

European Patent Application No. 407,811 A2 discloses an acetone cyanohydrin process that does not require sulfuric acid for preparing methacrylic acid esters. A key step of this process is the vapor phase dehydration/dealcoholization of α-hydroxy-, α-alkoxy, or β-alkoxy carboxylic acid esters in the presence of an alkali metal and platinum group element modified crystalline aluminosilicate disclosed in European Patent Application 429,800 A2. However, this process suffers from low yields based on ACH.

Even with the improved process described in '816, there is still a need for a high purity, high yield MMA process. Part of the driving force for additional improvements is the need to reduce waste products from currently practiced manufacturing processes.

SUMMARY OF THE INVENTION

The present invention is a method for producing α,β-unsaturated carboxylic acid esters in high yield through reduced formation of reaction side products and recycling of process intermediates.

DETAILED DESCRIPTION OF THE INVENTION

The present invention is a method for producing high purity (greater than about 99 weight percent) α,β-unsaturated carboxylic acid esters in high yield (greater than about 95 percent) based on the starting ACH by a modification of the conventional sulfuric acid/ACH process.

The modified process is conducted as follows:

1. Hydrolyze ACH with sulfuric acid to produce a hydrolysis mixture comprising MAM, SIBAM, HIBAM, and MAA under conditions of time and temperature such that the sum of the total moles of MAM, SIBAM, HIBAM, and MAA derived from ACH is maximized.
2. Esterify the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate, a $C_1$-$C_{12}$ alkyl β-$C_1$-$C_{12}$ alkoxyisobutyrate, and $C_1$-$C_{12}$ alkyl α-$C_1$-$C_{12}$ alkoxyisobutyrate.
3. Separate the esterification mixture into an aqueous fraction, a first organic fraction comprising $C_1$-$C_{12}$ alkyl methacrylate, and a second organic fraction comprising $C_1$-$C_{12}$ alkyl α-hydroxyisobutyrate, $C_1$-$C_{12}$ alkyl α-$C_1$-$C_{12}$ alkoxyisobutyrate, and $C_1$-$C_{12}$ alkyl β-$C_1$-$C_{12}$ alkoxyisobutyrate.
4. Dehydrate the components of the second organic fraction to produce a recycle mixture comprising $C_1$-$C_{12}$ alkyl methacrylate, methacrylic acid, $C_1$-$C_{12}$ alkyl alcohol, and water. For purposes of this disclosure, the term "dehydrate" or "dehydrated" means eliminating a water molecule from α- or β-hydroxy substituted components or eliminating an alkyl alcohol molecule from α- or β-alkoxy substituted components to produce α,β-unsaturated carboxylic acid esters.
5. Combine the recycle mixture with either the hydrolysis mixture, that is, between steps 1 and 2, or the esterification mixture, that is, between steps 2 and 3.

For illustrative purposes, the following description will be limited to a method for producing methyl methacrylate. However, the method is generally applicable to methacrylic acid esters prepared using the sulfuric acid/ACH process and $C_1$-$C_{12}$ alkyl alcohols. Use of alcohols of $C_1$-$C_4$ are preferred because of the commercial value of their methacrylate esters. The most preferred alcohol is methanol. The greatest yield loss in the process as currently practiced occurs during the thermal conversion of HIBAM to MAM prior to esterification. Since the thermal conversion of SIBAM to MAM is more facile than the conversion of HIBAM to MAM, SIBAM is a more desirable hydrolysis product. Because the formation of HIBAM from ACH results from the presence of water, typical commercial processes use $H_2SO_4$ with purifies approaching 100%. This minimizes the formation of HIBAM and maximizes the formation of SIBAM. The present invention eliminates the requirement for the thermal conversion of HIBAM to MAM. The net effect is to optimize the hydrolysis and dehydration steps based on a redefinition of the optimum pre-esterification yield as the sum of MAM, SIBAM, HIBAM, and MAA. Methods currently practiced in sulfuric acid/ACH processes strive to maximize only the sum of MAM and MAA prior to the esterification step. In the present invention, the thermal conversion of HIBAM and SIBAM to MAM is not required since the resulting esterified products, MOB, methyl β-methoxyisobutyrate ("β-MEMOB"), and methyl α-methoxyisobutyrate ("α-MEMOB"), are isolated and converted to MMA in a separate step. A second modification to the sulfuric acid/ACH process in the present invention is to dehydrate MOB, α-MEMOB, and β-MEMOB to MMA prior to recycling to the process. This is in contrast to the '816 process where the MOB is dehydrated, in lower yield, after recycling.

In this invention, ACH is hydrolyzed using excess sulfuric acid at a temperature from about 80° C. to about 135° C., preferably from about 80° C. to about 105° C., for a time sufficient to maximize the pre-esterification yield of the total of MAM, SIBAM, HIBAM, and MAA. The temperature can be maintained at a single value or changed during the course of the reaction. This may be accomplished either continuously or stepwise. The time required will vary from less than 1 minute to about 60 minutes. The sulfuric acid concentration is not critical. Concentrations of 95–100% are preferred, but 100% sulfuric acid is not required. The mole percent distribution of reacted ACH equivalent products in the process stream in the hydrolysis mixture will vary. However, conditions are preferred which result in the following distribution: about 60%–80% MAM; about 1–20% SIBAM; about 2%–20% HIBAM (more preferably 5% to 15%); and about 0%–5% MAA with an overall ACH conversion rate of about 100%. The advantage of this new process is that the yield loss incurred in the conventional process by efforts to reduce HIBAM levels during thermal conversion to MAM is reduced.

The MAM/SIBAM/HIBAM/MAA mixture is then esterified using any esterification procedure practiced on an industrial scale, such as, for example, mixing with excess aqueous alcohol using sulfuric acid as a catalyst under pressures of up to 100 psig at 100°–150° C. with residence times of generally less than 1 hour. In the case of MMA production, excess aqueous methanol is combined with the hydrolysis mixture. Esterification conditions are not critical and can be varied over a wide range. The only requirement is that the conditions be mild enough such that side reactions leading to degradation products do not occur to an unacceptable extent.

The esterification step produces an esterification mixture comprising MMA, MOB, α-MEMOB, and β-MEMOB along with significant quantities of water and unreacted methanol. This mixture is separated into an aqueous fraction and an organic fraction. The aqueous fraction contains varying amounts of the above components which may ultimately be recycled to the process. The organic fraction is separated into a number of additional fractions using standard separation techniques, but fractional distillation is preferred. Fractional distillation conditions are adjusted to give a forerun of low boiling components such as water, unreacted methanol, small amounts of MMA, and the like. Next, a first fraction comprising high purity MMA is obtained. Finally, a second fraction comprising higher boiling materials including MOB, α-MEMOB, and β-MEMOB, and the like, is obtained.

The isobutyrate-containing components of the second fraction are dehydrated, preferably in the vapor phase in the presence of a crystalline aluminosilicate, and more preferably, a crystalline aluminosilicate that has been modified with an alkali metal and platinum group element, to produce a recycle mixture. This mixture is recycled to the process. The dehydration step is performed on the components of the second fraction as is or, more preferably, in the presence of methanol and/or a diluting agent such as an inert gas, at reaction temperatures of from about 200° C. to about 400° C. Methanol aids in the prevention of by-product methacrylic acid formation.

One advantage of the present invention's modified process is that even though each individual step in the process is not conducted in a manner which would maximize the yield of MMA based on that particular step, the overall process maximizes the overall yield of MMA.

The advantage of the present invention over known methods is three-fold. First, it avoids the use of the typically harsh conditions needed in order to maximize the MAM yield in the thermal conversion step of the typical ACH process (step 2 of '816). Such conditions reduce the overall yield of the process due to side reactions such as, for example, the decomposition of MAM and any MAA which is present as a result of the hydrolysis of MAM or the dimerization of MAM, and the like. By reducing the severity of the thermal conversion conditions, the yield of MAM is also reduced due to the lower conversion of SIBAM and HIBAM to MAM. However, in subsequent steps, this excess SIBAM and HIBAM is esterified into α-MEMOB and MOB, dehydrated to MMA, and recycled to the process in a more efficient manner than obtained using the conventional thermal conversion of HIBAM to MAM. By recovering the MOB and α-MEMOB, converting them to MMA and MAA, and then recycling them to the process, there is an overall increase in the yield of MMA from the process as well as a reduction of waste material which must be disposed of by incineration, landfilling, or the like. Thus, the modified process results in a significant cost savings in terms of increased yield and reduced waste disposal over currently practiced processes.

A second advantage of the present invention is that β-MEMOB, a by-product produced in the esterification step, is easily isolated along with MOB and α-MEMOB. β-MEMOB is also converted to MMA. This lends to an additional yield improvement and another net reduction in process waste.

A third advantage of the present invention 'is that $H_2SO_4$ lower in purity than that used in currently practiced processes can be used in the present process. The formation of HIBAM from ACH results from the presence of $H_2O$. In fact, SIBAM is the more desirable hydrolysis product since the thermal conversion of SIBAM to MAM is more facile than the conversion of HIBAM to MAM. Typical commercial processes use $H_2SO_4$ purities approaching 100% to minimize the formation of HIBAM and minimize the yield loss incurred from the conditions necessary to thermally convert HIBAM to MAM. Since the thermal conversion of HIBAM is not required with this modified process, lower purity $H_2SO_4$, that is, higher levels of water, may be used.

The following examples illustrate the present invention in greater detail. They do not limit the invention in any way.

EXAMPLES

The following data demonstrate the increase in overall yield which may be expected in the conversion of ACH to MMA by comparing the changes in composition in the hydrolysis mixture expected by the process of this invention (Example—1) with that expected using a typical commercial process such as disclosed in the '816 patent (Comparative Example—2). The results for this invention are based on using a hydrolysis temperature of 105° C. for 35 minutes with a weight ratio of sulfuric acid to ACH of 1.7 to 1.0 (63 weight % sulfuric acid). The results for the '816 comparative example reflect pre-esterification compositions typically encountered in a commercial production facility. Representative expected results are in Table 1.

Comparative Example—2 shows an almost 20 mole % greater expected conversion to MAM than Example 1. However, this is at the expense of the expected overall total pre-esterification yield (MAM+MAA+HIBAM+SIBAM). In the present invention none of these four components is wasted rather, they are either converted to MMA in subsequent steps of the process or they are converted to other intermediates which are recycled to the process. Therefore, the overall yield of MMA is dramatically increased over that obtained using current commercial processes.

$C_1$–$C_{12}$ alkyl methacrylate, and a second organic fraction comprising the $C_1$–$C_{12}$ alkyl α-hydroxyisobutyrate, the $C_1$–$C_{12}$ alkyl β-$C_1$–$C_{12}$ alkoxyisobutyrate, and the $C_1$–$C_{12}$ alkyl α-$C_1$–$C_{12}$ alkoxyisobutyrate.

d. dehydrating the isobutyrate-containing components of the second organic fraction to produce a recycle mixture comprising a $C_1$–$C_{12}$ alkyl methacrylate, methacrylic acid, a $C_1$–$C_{12}$ alkyl alcohol, and water;

e. combining the recycle mixture with either the hydrolysis mixture or the esterification mixture.

2. The method of claim 1 in which the α-hydroxyisobutyramide concentration in the process stream just prior to esterification is about 2 to about 20 mole % based on the starting acetone cyanohydrin.

3. The method of claim 1 in which the α-hydroxyisobutyramide concentration in the process stream just prior to esterification is about 5 to about 15 mole % based on the starting acetone cyanohydrin.

4. The method of claim 1 in which the α-sulfatoisobutyramide concentration in the process stream

TABLE 1

| Example No. | Component | wt % in Stream | Stream Composition After Step 1 (Pre-esterification) Selectivity Based on ACH at 100% Conversion (mole %) | Pre-esterification Yield MAM + MAA + HIBAM + SIBAM | Overall Yield to MMA (Based on ACH) |
|---|---|---|---|---|---|
| 1: (This Invention) | | | | 97.3 | 95.6* |
| | H₂SO₄ | 63.0 | | | |
| | MAM | 25.8 | 69.9 | | |
| | HIBAM | 4.0 | 11.0 | | |
| | MAA | 0.1 | 0.3 | | |
| | SIBAM | 5.9 | 16.1 | | |
| | Others | 1.2 | 2.7 | | |
| 2: (Comparative Example from '816) | | | | 92.7 | 91.8** |
| | H₂SO₄ | 63.0 | | | |
| | MAM | 32.1 | 90.3 | | |
| | HIBAM | 1.3 | 1.3 | | |
| | MAA | 0.4 | 1.3 | | |
| | SIBAM | <0.1 | 0.1 | | |
| | Others | 3.2 | 7.3 | | |

*Calculated using an esterification yield of 99.5%, an isolation of the second organic fraction yield of 99.9%, and EP 429,800 A2 data of 99% conversion of the second organic fraction with a 96.6% yield to MMA and MAA.
**Calculated using an esterification yield of 99.5% and a 63.7% yield on MOB to MMA and MAA as described in '816.

We claim:

1. A method for producing methacrylic acid esters comprising the steps of;

a. hydrolyzing acetone cyanohydrin with sulfuric acid to produce a hydrolysis mixture comprising 2-methacrylamide, α-sulfatoisobutyramide, α-hydroxyisobutyramide, and methacrylic acid, wherein the sum of the total moles of these components derived from ACH is maximized;

b. esterifying the hydrolysis mixture with a $C_1$–$C_{12}$ alkyl alcohol to produce an esterification mixture comprising a $C_1$–$C_{12}$ alkyl methacrylate, a $C_1$–$C_{12}$ alkyl α-hydroxyisobutyrate, a $C_1$–$C_{12}$ alkyl β-$C_1$–$C_{12}$ alkoxyisobutyrate, and a $C_1$–$C_{12}$ alkyl α-$C_1$–$C_{12}$ alkoxyisobutyrate;

c. separating the esterification mixture into an aqueous fraction, a first organic fraction comprising the just prior to esterification is from about 1 to about 20 mole % based on the starting acetone cyanohydrin.

5. The method of claim 1 wherein the $C_1$–$C_{12}$ alkyl alcohol is selected from methanol, ethanol, n-propanol, isopropanol, n-butanol, and isobutanol.

6. The method of claim 1 wherein the $C_1$–$C_{12}$ alkyl alcohol is methanol.

7. The method of claim 1 wherein the separating step comprises fractional distillation of the esterification mixture.

8. The method of claim 1 wherein the dehydrating step is conducted in the vapor phase in the presence of a crystalline aluminosilicate.

9. The method of claim 8 wherein the crystalline aluminosilicate is modified with an alkali metal and a platinum group element.

* * * * *